United States Patent [19]

Duranleau et al.

[11] Patent Number: 4,565,866
[45] Date of Patent: Jan. 21, 1986

[54] METHOD FOR THE PREPARATION OF FORMAMIDES

[75] Inventors: Roger G. Duranleau, Georgetown; John F. Knifton; George P. Speranza, both of Austin, all of Tex.

[73] Assignee: Texaco Inc., White Plains, N.Y.

[21] Appl. No.: 573,443

[22] Filed: Jan. 24, 1984

[51] Int. Cl.$^4$ .................. C07C 102/00; C07D 265/30; C07D 241/04
[52] U.S. Cl. .................................... 544/176; 544/386; 544/387; 564/132
[58] Field of Search ................ 564/132; 544/176, 386, 544/387

[56] References Cited

U.S. PATENT DOCUMENTS 4,098,820 7/1978 Couteau et al. ............. 564/132
4,140,716 2/1979 Maender et al. ............. 564/132 X Primary Examiner—Thomas A. Waltz
Assistant Examiner—Carolyn Greason
Attorney, Agent, or Firm—R. A. Kulason; Jack H. Park; Cynthia L. Kendrick

[57] ABSTRACT

The instant invention relates to a process for the preparation of formamides in which ammonia, a primary or a secondary amine is reacted with carbon monoxide at an elevated temperature and pressure in the presence of a mixture consisting of a phenol and a phenate salt from the group consisting of an alkali metal phenate and an alkaline earth metal phenate, said phenol and said phenate salt each having the radical:

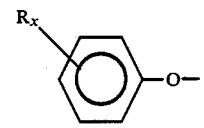

wherein R is selected from the group consisting of an alkyl radical having from 3 to 18 carbon atoms and a hydroxyaryl radical of the formula:

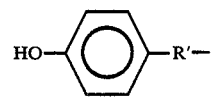

in which R' is an alkylene group having from 2 to 5 carbon atoms and in which x has a value of 1 to 2 when R is said alkyl radical and x has a value of 1 when R is said hydroxyaryl radical.

17 Claims, No Drawings

METHOD FOR THE PREPARATION OF FORMAMIDES

FIELD OF THE INVENTION

This invention relates to a process for the preparation of formamide compounds in which the corresponding nitrogen compound and carbon monoxide are reacted in the presence of a mixture consisting of a phenol and a phenate salt from the group consisting of an alkali metal phenate or an alkaline earth metal phenate. The process of the instant invention can be employed to prepare dimethylformamide, formamide, and morpholine formamide, compounds which have considerable commercial value.

BACKGROUND OF THE INVENTION

A well known process for preparing formamide compounds involves reacting the corresponding amine with carbon monoxide in the presence of sodium methoxide in a methanolic solution, see Kirk-Othmer, *Encyclopedia of Chemical Technology* (3rd Edition, Volume 11) at pages 259 and 264 thru 265. A serious problem with this process is that sodium methoxide strongly catalyzes the reverse reaction as well as the (forward) desired reaction. Elaborate processing schemes have been employed to prevent the sodium methoxide catalyst from contacting the formed product. Another problem is that the sodium methoxide catalyst and the corresponding formate formed when the sodium methoxide catalyst reacts with carbon monoxide in the presence of water both tend to precipitate out of solution. The formed solid deposits clog the pipes and valves of the apparatus used in the process.

It is an object of this invention to provide an improved process for the preparation of formamides in which the carbonylation of amines is accomplished employing a novel catalyst system.

INFORMATION DISCLOSURE STATEMENT

U.S. Pat. No. 4,098,820 discloses a method for preparing formamide compounds by heating the corresponding amine and carbon monoxide in the presence of a methanolic solution of an alkali metal or alkaline earth metal methylate catalyst.

SUMMARY OF THE INVENTION

The instant invention relates to a process for the preparation of formamides in which ammonia, a primary or a secondary amine is reacted with carbon monoxide at an elevated temperature and pressure in the presence of a mixture consisting of a phenol and a phenate salt from the group consisting of an alkali metal phenate and an alkaline earth metal phenate, said phenol and said phenate salt each having the radical:

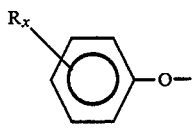

wherein R is selected from the group consisting of an alkyl radical having from 3 to 18 carbon atoms and a hydroxyaryl radical of the formula:

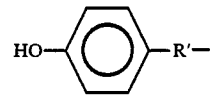

in which R' is an alkylene group having from 2 to 5 carbon atoms and in which x has a value of 1 to 2 when R is said alkyl radical and x has a value of 1 when R is said hydroxyaryl radical.

DETAILED DESCRIPTION OF THE INVENTION

It has now been discovered that ammonia, a primary or a secondary amine and carbon monoxide can be reacted to prepare formamides in the presence of a mixture consisting of a phenol and a phenate salt from the group consisting of an alkali metal phenate and an alkaline earth metal phenate.

The phenol employed can be mono-substituted with an alkylphenol radical, or mono- or di-substituted with an alkyl radical. Suitable alkyl radicals include straight or branch chained alkyl groups having from 1 to 15 carbon atoms such as methyl, ethyl, isopropyl, butyl, t-butyl, pentyl, isopentyl, hexyl, amyl, octyl, and nonyl. Suitable alkylphenol radicals include those having a straight or branch chained alkyl substituent of from 2 to 5 carbon atoms. Also substituted phenols having more than one fused aromatic ring, such as naphthols, anthranols and phenanthranols, may be employed.

The preferred phenol is represented by the formula:

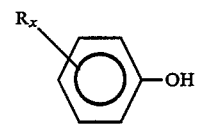

wherein R is selected from the group consisting of an alkyl radical having from 3 to 18 carbon atoms and a hydroxyaryl radical having the formula:

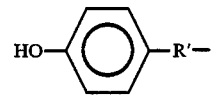

in which R' is an alkylene group having from 2 to 5 carbon atoms and in which x has a value of 1 to 2 when R is said alkyl radical and x has a value of 1 when R is said hydroxyaryl radical.

The most preferred phenol is represented by the formula:

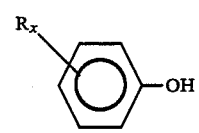

wherein R is selected from the group consisting of an alkyl radical having from 6 to 15 carbon atoms and a hydroxyaryl radical having the formula:

in which R' is an alkylene radical having from 2 to 3 carbon atoms and in which x has a value of 1 to 2 when R is said alkyl radical and x has a value of 1 when R is said hydroxyaryl radical. Examples of the most preferred phenols include nonylphenol, di-nonylphenol, and 2,2-bis(4-hydroxyphenol)propane (bisphenol A).

The phenate salt is prepared by reacting the prescribed phenols with a Group 1A and Group 2A metals or metal salts to form a corresponding alkali metal phenate or alkaline earth metal phenate. The most preferred phenate is an alkali metal salt or an alkaline earth metal salt of a phenol represented by the formula:

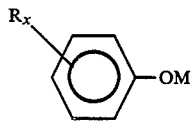

wherein R is selected from the group consisting of an alkyl radical having 6 to 12 carbon atoms and a hydroxyaryl radical having the formula:

in which R' is an alkylene radical having from 2 to 3 carbon atoms, in which x has a value of 1 to 2 when R is said alkyl radical and x has a value of 1 when R is said hydroxyaryl radical and M is the metal equivalent of an alkali or an alkaline earth metal.

Typically, an alkali metal, such as sodium, is employed but other alkali metals are equally effective. Also, alkaline earth metals such as calcium and barium can be employed. The alkali metal phenate or alkaline earth metal phenate need not be derived from the same compound as the phenol component. Mixtures of phenol and alkali metal phenate or alkaline earth metal phenate from the prescribed class of phenols and the prescribed class of alkali metal phenates or alkaline earth metal phenates are suitable. For example, an effective mixture for promoting the reaction can consist of nonylphenol and an alkali metal phenate or alkaline earth metal phenate of di-nonylphenol. Preferably, the corresponding phenol is employed to prepare the alkali metal phenate or alkaline earth metal phenate. Generally, the mixture will comprise from about 60 to about 90 weight percent of the phenol component and from 40 to 10 weight percent of an alkali metal phenate or alkaline earth metal phenate component.

Two classes of nitrogen compounds can be reacted in the instant process. The first class of compounds is represented by the formula:

wherein R is hydrogen or an alkyl radical having from 1 to 10 carbon atoms and R' is selected from the group consisting of hydrogen, an alkyl or an alkylene radical having from 1 to 10 carbon atoms, a cyclohexyl, a phenyl radical, an aminoalkyl or an aminoalkylene radical having from 1 to 10 carbon atoms, or R''—O—R''', wherein R'' is a divalent alkylene radical of 2 to 4 carbon atoms and R''' is an alkyl radical of 1 to 3 carbon atoms. Preferred compounds in this class are those in which R and R' have from 1 to 5 carbon atoms.

The second class of compounds which can be reacted in this process are represented by the formula:

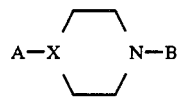

wherein X is oxygen or nitrogen.

A is hydrogen when X is nitrogen but is not present when X is oxygen.

B is hydrogen.

Suitable primary or secondary amines include aniline, ethylamine, propylamine, butylamine, pentylamine, hexylamine, octylamine, nonylamine, decylamine, ethylenediamine, propylenediamine, butylenediamine, pentylenediamine, hexylenediamine, cyclohexylamine, methoxypropylamine, ethoxypropylamine, propoxypropylamine, dimethylamine, diethylamine, dipropylamine, dibutylamine, ethylmethylamine, ethylpropylamine and propylbutylamine. Suitable cyclic amines include morpholine and piperazine.

The precursor nitrogen compound and carbon monoxide react at a temperature ranging from about 50° C. to about 300° C., and a pressure ranging from about 100 to about 10,000 psig. Preferably, the reaction temperature employed ranges from about 100° to about 250° C. and the pressure ranges from about 200 to about 5,000 psig, and most preferably a temperature from about 140° to about 200° C. and a pressure from about 400 to about 2,500 psig. The mixture of a phenol and alkali metal phenate or alkaline earth metal phenate promoter is employed in the reaction at a concentration from about 0.2 to about 4% and preferably from about 0.4 to about 2.5% by weight of the precursor nitrogen compound employed.

The carbon monoxide employed can be relatively pure or can comprise a mixture of carbon monoxide and other gases which are inert under the reaction conditions of the process, such as hydrogen, nitrogen, and saturated hydrocarbons. The carbon monoxide content in the gas should range from at least 20 to 100% by volume and preferably from about 50 to 100% by volume. Gas streams from synthesis gas processing units do not have to be pretreated and may be employed directly without effecting carbon monoxide separation and purification. Particular care should be taken to insure that the gas containing carbon monoxide contains the smallest possible amount of water, for example, less than 5 ppm, as water reacts with the salt to form a precipitate of an alkali metal or alkaline earth metal formate.

Reacting carbon monoxide with ammonia, a primary or a secondary amine in the presence of a mixture consisting of a phenol and an alkali metal phenate or an alkaline earth metal phenate to prepare formamides offers numerous advantages: first, the rate of product formation in a continuous reaction process can be controlled by adjusting the amount of alkali metal or alkaline earth metal phenate salt present in the reaction;

second, the precursor nitrogen compound, the formamide product, and the catalyst system are soluble in each other, forming a homogeneous liquid which is easily handled. Further, because the mixture has a relatively high boiling point, the formamide product can be recovered by distillation and the remaining bottoms containing the phenol and alkali metal and alkaline earth metal phenate salt can be recycled and used again.

The following examples illustrate the practice of this invention.

EXAMPLE I

PREPARATION OF FORMYLMORPHOLINE 500 grams (5.75 moles) of morpholine was reacted with carbon monoxide in the presence of a mixture of 133.8 grams (0.608 moles) of nonylphenol and 57.8 grams (0.239 moles) of sodium nonylphenate in a stainless steel autoclave equipped with a stirrer. After being flushed with carbon monoxide, the autoclave was sealed, carbon monoxide introduced, and the contents heated to 110° C. at a pressure of 1,300 psig. The autoclave was periodically repressurized with carbon monoxide to replenish the carbon monoxide that was consumed. The reaction was stopped after 5 hours. Gas chromographic analysis of the reaction product demonstrated that 20% of the initial morpholine charged was consumed and that the predominate product formed in the reaction was formylmorpholine. Measured as the percentage of consumed morpholine converted to formylmorpholine product, the product selectivity was 97.9%.

EXAMPLE II 500 grams (5.75 moles) of morpholine was reacted with carbon monoxide in the presence of a mixture of 133.8 grams (0.608 moles) of nonylphenol and 57.8 grams (0.239 moles) of sodium nonylphenate as in Example I, except that the reaction was conducted for seven hours at a temperature of 170° C. and a carbon monoxide pressure of 2,000 psig. The 802 grams of liquid product were distilled in a short (2") distillation apparatus at a pressure of 7-10 mm Hg and a pot temperature not greater than 150° C. Gas chromographic analysis indicated that the first cut (541.0 grams) contained 528.5 grams of formylmorpholine, that the second cut (112.0 grams) contained 57.2 grams of formylmorpholine and 54.8 grams of nonylphenol, and that the bottoms portion (129 grams) contained 4.0 grams of formylmorpholine. All of the charged morpholine was consumed and 95.9% of the consumed morpholine was converted to formylmorpholine.

EXAMPLE III 450 grams (5.17 moles) of morpholine was reacted with carbon monoxide in the presence of 34.2 grams (0.15 moles) of bisphenol A (2,2-bis(4-hydroxyphenol)-propane) and 87.5 grams (0.35 moles) of sodium bisphenate as in Example II, except that the reaction was stopped after 5.5 hours. Gas chromographic analysis revealed that the liquid product (787 grams) comprised a substantial amount (81.6%) of formylmorpholine.

EXAMPLE IV 100 grams (1.15 moles) of morpholine was reacted with carbon monoxide in the presence of a mixture of 25 grams (0.0723 moles) of dinonylphenol and 25 grams (0.068 moles) of sodium dinonylphenate as in Example II, except that the reaction was stopped after five hours. 181.2 grams of formed solid product were recovered. Gas chromographic and NMR analysis indicated that greater than 99% of the initial morpholine charged was consumed and that 99% of the consumed morpholine was converted to formylmopholine.

EXAMPLE V

RECYCLING OF BOTTOMS FRACTION 500 grams (5.75 moles) of morpholine was reacted with carbon monoxide as in Example II, except that the reaction was conducted in the presence of the bottoms fraction produced in Example II to which had been added 47 grams of nonylphenol and 13 grams of formylmorpholine. Gas chromographic analysis of the product indicated that all of the charged morpholine was consumed and 97% of the consumed morpholine was converted to formylmorpholine.

EXAMPLE VI

CONTINUOUS RUN 7,684 grams (8.3 moles) of morpholine and carbon monoxide were continuously reacted in the presence of 2,003 grams (9.1 moles) of nonylphenol and 549.3 grams (2.27 moles) of the sodium nonylphenate in an autoclave equipped with a stirrer. The feed was passed into the autoclave at a rate of 300 ml/hr., the reaction temperature was 190° C., and the carbon monoxide pressure was 1,500 psig. Analysis of the reaction product indicated that 89% of the initial morpholine charged was consumed and that 100% of the consumed morpholine was converted to formylmorpholine. The productivity was 0.89 g/cc reactor vol/hour.

EXAMPLE VII-XVI

PREPARATION OF VARIOUS FORMAMIDE PRODUCTS

A number of different amines were reacted with carbon monoxide in the presence of a phenol and an alkali metal phenate or alkaline earth metal phenate salt as in Example I. The details of the process conditions are given in Table I below.

TABLE I

| Ex. # | Amine | Moles Amine | Moles Nonyl-phenol | Moles Sodium Nonyl-phenate | Temp °C. | Carbon Monoxide Pressure psig | Holding time | Product | Moles Product | % Amine Conv. | % Prod. Select. |
|---|---|---|---|---|---|---|---|---|---|---|---|
| VII | Piperazine | 4.65 | 0.30 | 0.14 | 190 | 2,500 | 13 hr. | 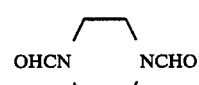 OHCN NCHO | 4.64 | 100 | 99.7 |

TABLE I-continued

| Ex. # | Amine | Moles Amine | Moles Nonyl-phenol | Moles Sodium Nonyl-phenate | Temp °C. | Carbon Monoxide Pressure psig | Holding time | Product | Moles Product | % Amine Conv. | % Prod. Select. |
|---|---|---|---|---|---|---|---|---|---|---|---|
| VIII | Piperazine | 4.65 | 0.30 | 0.14 | 170 | 2,000 | 13 hr. | HN⟨ ⟩NCHO, OHCN⟨ ⟩NCHO | 3.63 | 78 | 78.0 |
| IX | Octylamine | 0.774 | 0.179 | 0.045 | 175 | 2,000 | 6.25 hr. | C₈H₁₇NHCHO | 0.76 | 100 | 98.0 |
| X | Aniline | 1.08 | 0.179 | 0.045 | 195 | 2,000 | 7.5 hr. | C₆H₅-NCHO | 0.87 | 81 | 81.0 |
| XI | Ethylene-diamine | 1.5 | 0.179 | 0.045 | 175 | 2,000 | 13.0 hr. | H₂NCH₂CH₂NHCHO, OHCNHCH₂CH₂NHCHO | 1.5 | 100 | 99.0 |
| XII | Cyclo-hexylamine | 0.92 | 0.179 | 0.045 | 175 | 2,000 | 6.0 hr. | 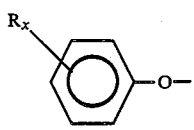 | 0.46 | 50 | 50.0 |
| XIII | Methoxy-propyl-amine | 1.12 | 0.179 | 0.045 | 170 | 2,000 | 7.0 hr. | CH₃OCH₂CH₂CH₂NHCHO | 1.12 | 100 | 100 |
| XIV | Dimethyl-amine | 1.0 | 0.179 | 0.045 | 170 | 2,000 | 5.0 hr. | (CH₃)₂NCHO | 2.0 | 100 | 90 |
| XV | Triethyl-amine | 1.0 | 0.179 | 0.045 | 191 | 2,075 | 7.0 hr. | None | 0 | 0 | 0 |
| XVI | Ammonia | 2.35 | 0.179 | 0.045 | 190 | 2,500 | 13.1 hr. | H₂NCHO | 2.21* | 85* | 94 |

*Estimated from weight gain.

The foregoing data demonstrate that ammonia and the prescribed nitrogen compounds react with carbon monoxide in the presence of a mixture consisting of an phenol and an alkali metal phenate or alkaline earth metal phenate to produce high yields of formamide products in both batch and continuous process runs. It was surprising that the mixture of a phenol and an alkali metal or an alkaline earth metal phenate salt would be effective for the carbonylation of ammonia and the noted nitrogen compounds.

What is claimed is:

1. In a process for the preparation of formamide and N-substituted formamides in which ammonia, a primary or a secondary amine is reacted with carbon monoxide at an elevated temperature and pressure, the improvement which comprises conducting said reaction in the presence of a mixture consisting of a phenol and a phenate salt from the group consisting of an alkali metal phenate and an alkaline earth metal phenate, said phenol and said phenate salt each having the radical:

$R_x$-C₆H₄-O— wherein R is selected from the group consisting of an alkyl radical having from 3 to 18 carbon atoms and a hydroxyaryl radical having the formula:

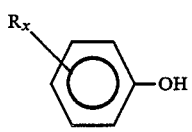

in which R' is a alkylene radical having from 2 to 5 carbon atoms and in which x has a value of 1 to 2 when R is said alkyl radical and x has a value of 1 when R is said hydroxyaryl radical.

2. A process according to claim 1 in which said phenol is represented by the formula:

$R_x$-C₆H₄-OH in which R is selected from the group consisting of an alkyl radical having from 6 to 15 carbon atoms and a hydroxyaryl radical having the formula:

in which R' is an alkylene radical having from 2 to 3 carbon atoms and in which x has a value of 1 to 2 when R is said alkyl radical and x has a value of 1 when R is said hydroxyaryl radical.

3. A process according to claim 1 in which said phenol is selected from the group consisting of nonylphenol, di-nonylphenol, and 2,2-bis(4-hydroxyphenol)propane.

4. A process according to claim 1 in which said phenol is nonylphenol.

5. A process according to claim 1 in which said phenol is di-nonylphenol.

6. A process according to claim 1 in which said phenol is 2,2-bis(4-hydroxyphenol)propane.

7. A process according to claim 1 in which said alkali metal salt or alkaline earth metal salt of a phenol is represented by the formula:

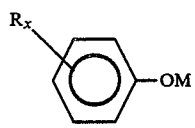

in which R is selected from the group consisting of an alkyl radical having from 6 to 15 carbon atoms and a hydroxyaryl radical having the formula:

in which R' is an alkylene radical having from 2 to 3 carbon atoms, x has a value from 1 to 2 when R is said alkyl radical and a value of 1 when R is said hydroxyaryl radical and M is the metal equivalent of alkali or alkaline earth metal.

8. A process according to claim 7 in which said metal is sodium.

9. A process according to claim 1 in which said mixture comprises from about 60 to 90 weight percent of said phenol and from about 40 to 10 weight percent of said alkali metal or alkaline earth metal phenate.

10. A process according to claim 1 wherein said temperature employed ranges from about 100° to about 250° C. and said pressure ranges from about 200 to about 5,000 psig.

11. A process according to claim 1 wherein said temperature employed ranges from about 140° to about 200° C. and said pressure ranges from about 400 to about 2,500 psig.

12. A process according to claim 1 wherein said amine is selected from the group consisting of amines having the formula:

$$\overset{R}{\underset{|}{H-N-R'}}$$     I in which R is hydrogen or an alkyl radical having from 1 to 10 carbon atoms and R' is selected from the group consisting of hydrogen, an alkyl or an alkylene radical having from 1 to 10 carbon atoms, a cyclohexyl, a phenyl radical, an aminoalkyl or an aminoalkylene radical having from 1 to 10 carbon atoms, or a R''—O—R''' radical wherein R'' is a divalent alkylene radical of 2 to 4 carbon atoms and R''' is an alkyl radical of 1 to 3 carbon atoms, and amines having the formula:

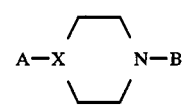

wherein X is oxygen or nitrogen and wherein A is hydrogen when X is nitrogen, but is not present when X is oxygen and B is hydrogen.

13. A process for the preparation of formamide in which ammonia is reacted with carbon monoxide at an elevated temperature and pressure, the improvement which comprises conducting said reaction in the presence of a mixture consisting of a phenol and a phenate salt from the group consisting of an alkali metal phenate and an alkaline earth metal phenate, said phenol and said phenate salt each having the radical:

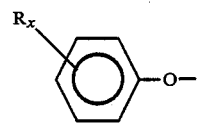

wherein R is selected from the group consisting of an alkyl radical having from 6 to 15 carbon atoms and a hydroxyaryl radical having the formula:

in which R' is a alkylene radical having from 2 to 3 carbon atoms and in which x has a value of 1 to 2 when R is said alkyl radical and x has a value of 1 when R is said hydroxyaryl radical.

14. A process for the preparation of di-methylformamide in which dimethylamine is reacted with carbon monoxide at an elevated temperature and pressure, the improvement which comprises conducting said reaction in the presence of a mixture consisting of a phenol and a phenate salt selected from the group consisting of an alkali metal phenate and an alkaline earth metal phenate, said phenol and said phenate salt each having the radical:

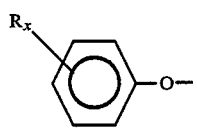

wherein R is selected from the group consisting of an alkyl radical having from 6 to 15 carbon atoms and a hydroxyaryl radical having the formula:

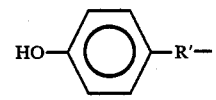

in which R' is a alkylene radical having from 2 to 3 carbon atoms and in which x has a value of 1 to 2 when R is said alkyl radical and x has a value of 1 when R is said hydroxyaryl radical.

15. A process for the preparation of morpholine formamide in which morpholine is reacted with carbon monoxide at an elevated temperature and pressure, the improvement which comprises conducting said reaction the presence of a mixture consisting of a phenol and a phenate salt selected from the group consisting of an alkali metal phenate and an alkaline earth metal phenate, said phenol and said phenate salt each having the radical:

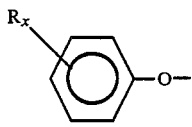

wherein R is selected from the group consisting of an alkyl radical having from 6 to 15 carbon atoms and a hydroxyaryl radical having the formula:

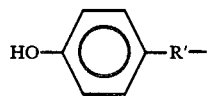

in which R' is a alkylene radical having from 2 to 3 carbon atoms and in which x has a value of 1 to 2 when R is said alkyl radical and x has a value of 1 when R is said hydroxyaryl radical.

16. In a process for the preparation of formamide and N-substituted formamides in which ammonia, a primary or a secondary amine is reacted with carbon monoxide at an elevated temperature and pressure, the improvement which comprises conducting said reaction in the presence of a mixture consisting of a phenol represented by the formula:

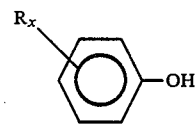

wherein R is selected from the group consisting of an alkyl radical having from 6 to 15 carbon atoms and a hydroxyaryl radical having the formula:

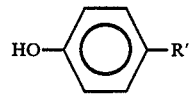

wherein R' is an alkylene radical having from 2 to 3 carbon atoms and x has a value of 1 to 2 when R is said alkyl radical and x has a value of 1 when R is said hydroxyaryl radical and a phenate salt from the group consisting of an alkali metal phenate and an alkaline earth metal phenate, said phenate salt having the radical:

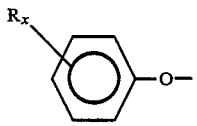

wherein R is selected from the group consisting of an alkyl radical having from 3 to 18 carbon atoms and a hydroxyaryl radical having the formula:

wherein R' is an alkylene radical having from 2 to 5 carbon atoms and in which x has a value of 1 to 2 when R is said alkyl radical and x has a value of 1 when R is said hydroxyaryl radical.

17. A process according to claim 16 wherein in R said alkyl radical has from 1 to 5 carbon atoms and in R' said alkyl or alkylene radical has from 1 to 5 carbon atoms and said aminoalkyl or aminoalkylene radical has from 1 to 5 carbon atoms.

* * * * *